United States Patent [19]

Stähle et al.

[11] 4,341,788

[45] Jul. 27, 1982

[54] 2-(2-CHLORO-4-CYCLOPROPYL-PHENYL-IMINO)-IMIDAZOLIDINE, AND ACID ADDITION SALTS THEREOF AS BRADYCARDIACS

[75] Inventors: Helmut Stähle; Herbert Köppe; Werner Kummer, all of Ingelheim am Rhein; Wolfgang Hoefke, Wiesbaden, all of Fed. Rep. of Germany; Ludwig Pichler, Vienna, Austria

[73] Assignee: C. H. Boehringer Sohn, Ingelheim am Rhein, Fed. Rep. of Germany

[21] Appl. No.: 253,860

[22] PCT Filed: Aug. 20, 1980

[86] PCT No.: PCT/EP80/00081

§ 371 Date: Apr. 15, 1981

§ 102(e) Date: Apr. 15, 1981

[87] PCT Pub. No.: WO81/00565

PCT Pub. Date: Mar. 5, 1981

[30] Foreign Application Priority Data

Aug. 22, 1979 [DE] Fed. Rep. of Germany ....... 2933930

[51] Int. Cl.$^3$ .................. A61K 31/415; C07D 233/50
[52] U.S. Cl. .................................. 424/273 R; 548/315; 564/105; 564/245; 564/271; 564/276
[58] Field of Search ..................... 548/315; 424/273 R

[56] References Cited

U.S. PATENT DOCUMENTS 4,290,971  9/1981  Georgien et al. ............... 548/315 X

FOREIGN PATENT DOCUMENTS 632578 11/1963 Belgium ............................. 548/315
462824  1/1950 Canada .............................. 548/315
  1663  5/1979 European Pat. Off. .

Primary Examiner—Richard A. Schwartz
Attorney, Agent, or Firm—Hammond & Littell, Weissenberger and Muserlian

[57] ABSTRACT

This invention is directed to 2-(2-chloro-4-cyclopropyl-phenyl-imino)-imidazolidine, and acid addition salts thereof, the preparation of said compounds, and the use of said compounds as bradycardiacs.

3 Claims, No Drawings

2-(2-CHLORO-4-CYCLOPROPYL-PHENYL-IMINO)-IMIDAZOLIDINE, AND ACID ADDITION SALTS THEREOF AS BRADYCARDIACS

The present invention relates to 2-(2-chloro-4-cyclopropyl-phenylimino)-imidazolidine of the formula:

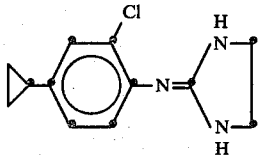

and the physiologically acceptable acid addition salts thereof, having valuable therapeutical properties.

The compound of formula I and the acid addition salts thereof may be prepared by one of the following processes (a) to (c):

(a) reacting a compound of the formula:

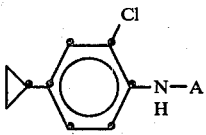

(wherein A represents a cyano group or the radical

in which Y represents an alkoxy or alkylthio group having 1 to 4 carbon atoms or a sulfhydryl or amino group) with ethylene diamine or an acid addition salt thereof.

The reaction is effected at a temperature of from 100° to 250° C. Polar protic, polar aprotic or non-polar solvents may be used as solvent. The reaction may, however be effected without the use of a solvent in which case the reaction is effected at an elevated temperature. The reaction time varies from a few minutes to several hours.

(b) reaction of a compound of the formula:

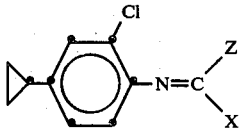

(wherein X and Z, which may be the same or different, each represent a halogen atom or an alkoxy or alkylthio group with 1 to 4 carbon atoms) with ethylene diamine or an acid addition salt thereof. If X and Z represent a halogen atom, preferably a chlorine atom, the reaction is effected at a temperature of from 0° C. to ambient temperature. Inert solvents such as for example ethers, ketones, esters or aliphatic or aromatic hydrocarbons may be used as solvent.

If X and Z represent alkoxy or alkylthio group, the reaction is effected at an elevated temperature, preferably at the reflux temperature of the reaction mixture. Polar protic, polar aprotic or non-polar solvents may be used as solvent.

(c) deacylation of a compound of the formula:

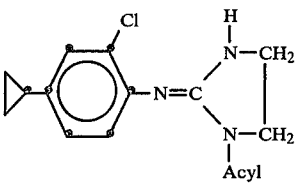

(wherein Acyl represents an aliphatic or aromatic acyl group) by reaction with an aliphatic alcohol or a dilute mineral acid.

Compounds of formula II may be obtained reacting 2-chloro-4-cyclopropylaniline with a cyanate or thiocyanate, a urea or thiourea being formed. The urea or thiourea may then be converted into the corresponding isouronium salt or isothiouronium salt for example, by the use of an alkylating agent. The corresponding isourea or isothiourea may be obtained from these acid addition compounds with bases. By dehydration of the urea or by removal of H$_2$S from the thiourea in the presence of lead or mercury salts 2-chloro-4-cyclopropyl-phenylcyanamide is obtained, with which ammonia may be reacted to form 2-chloro-4-cyclopropyl-phenyl-guanidine.

The isocyanide dichloride of formula III may be obtained by reaction of 2-chloro-4-cyclopropylaniline with formic acid followed by reaction of the formanilide obtained with a mixture of thionyl chloride and sulphuryl chloride.

Other starting compounds of formula III may be obtained by reacting the isocyanide dichloride with an alcohol or thioalcohol.

The starting compounds of formula IV may be prepared by reacting 2-chloro-4-cyclopropylaniline with an N-acyl-imidazolidinone-(2) in the presence of phosphorus oxychloride.

The 2-phenylimino-imidazolidine of the present invention may, if desired, be converted into a physiologically compatible acid addition salt by convertional methods. Acids suitable for salt formation include for example hydrochloric acid, hydrobromic acid, hydroiodic acid, hydrofluoric acid, sulphuric acid, phosphoric acid, nitric acid, acetic acid, propionic acid, butyric acid, caproic acid, valeric acid, oxalic acid, malonic acid, succinic acid, maleic acid, fumaric acid, lactic acid, tartaric acid, citric acid, malic acid, benzoic acid, p-hydroxybenzoic acid, p-aminobenzoic acid, phthalic acid, cinnamic acid, salicyclic acid, ascorbic acid, methanesulphonic acid and 8-chlorotheophylline.

The novel compound of formula I and the physiologically compatible acid addition salts possess a strong bradycardiac activity and are suitable for the treatment of coronary diseases. The influence of the said compound on the heart beat frequency has been investigated in rabbits and in pithed rats as well as in live anaesthetised rats.

The dosage ranges from 0.1 to 80 mgm, preferably from 1 to 30 mgm.

The compound of formula I as well as the acid addition salts thereof may also be combined with other active ingredients. Suitable pharmaceutical compositions include e.g. tablets, capsules, suppositories, solutions or powders. For the preparation of pharmaceutical compositions conventional excipients, carriers, disintegrants or lubricants or agents for obtaining sustained release may be used.

The following Examples illustrate the invention without restricting its scope:

EXAMPLE 1

2-(2-chloro-4-cyclopropyl-phenylimino)-imidazolidine

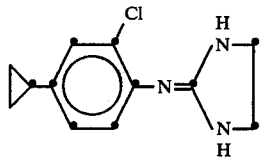

Molecular weight: 235.7
Molecular formula: $C_{12}H_{14}ClN_3$
Melting point: 133.5°–138.5° C.

| Elementary analysis: | C | H | Cl | N |
|---|---|---|---|---|
| Calculated | 61.15 | 5.99 | 15.04 | 17.83 |
| Found | 61.07 | 6.05 | 15.42 | 17.66 |

(a)
N-(2-chloro-4-cyclopropyl-phenyl)-S-methyl-isothiouronium iodide

4-Cyclopropylaniline is acetylated to 4-cyclopropyl-acetanilide (m.p. 111°–113.5° C.) and is chlorinated and saponified to 2-chloro-4-cyclopropylaniline as described in J. Amer. Chem. Soc. 62 (1940), 2103. The title compound is obtained by reaction of the aniline with ammonium thiocyanate followed by methylation of the resulting N-(2-chloro-4-cyclopropyl-phenyl)-thiourea with methyl iodide.

(b)
2-(2-chloro-4-cyclopropyl-phenylimino)-imidazolidine 8.30 g of N-(2-chloro-4-cyclopropyl-phenyl)-S-methyl-isothiouronium iodide are refluxed for 15 hours in 25 ml of methanol together with 2.3 ml (150%) of ethylene diamine. The clear reaction mixture is then evaporated in vacuo and a honey-like residue is left. This is dissolved in 1 N HCl and the hydrochloric acid solution is extracted twice with ether. The aqueous phase is subsequently buffered to pH 6 with 2 N NaOH and extracted with ether (50-ml portions) in fractions with rising pH values (fractioned alkalisation with 2 N NaOH). The approximately uniform ether fractions are combined (by a thin-layer chromatogram check), dried over MgSO$_4$ and evaporated in vacuo. For further purification the crude 2-(2-chloro-4-cyclopropyl-phenylimino)-imidazolidine is chromatographed over silica gel.

Eluant: isopropanol:ethyl acetate:concentrated ammonia=50:50:1. Yield: 1.3 g (corresponding to 23.6% of theory).

Melting point: 135.5° to 138.5° C.
Thin-layer chromatogram
System: isopropanol:ethyl acetate:concentrated ammonia (50:50:1).
Carrier: silical gel plates by Merck-Darmstadt No. 60F254.
Detector: (a) UV, (b) potassium iodoplatinate according to Schlittler.
Rf: 0.3.

PHARMACEUTICAL COMPOSITION EXAMPLES

Example A: Coated tablets

| Active substance according to invention | 5 mg |
|---|---|
| Lactose | 65 mg |
| Corn starch | 130 mg |
| Secondary calcium phosphate | 40 mg |
| Soluble starch | 3 mg |
| Magnesium stearate | 3 mg |
| Colloidal silicic acid | 4 mg |
| Total | 250 mg |

Preparation

The active substance is mixed with a part of the excipients, kneaded intensively with an aqueous solution of the soluble starch and granulated in conventional manner by means of a sieve. The granulate is mixed with the rest of the excipients and pressed into coated tablet cores weighing 250 mg which are then coated in a conventional manner with a coating of sugar, talcum and gum arabic.

Example B: Ampoules

| Active substance according to the invention | 1.0 mg |
|---|---|
| Sodium chloride | 18.0 mg |
| Distilled water sufficient to make | 2.0 ml |

Preparation

The active substance and sodium chloride are dissolved in water and filled, under nitrogen, into glass ampoules.

Example C: Drops

| Active substance according to the invention | 0.02 g |
|---|---|
| Methyl-p-hydroxybenzoate | 0.07 g |
| Methyl-p-hydroxybenzoate | 0.03 g |
| Demineralised water sufficient to make | 100 ml |

What we claim is:
1. A compound of the formula

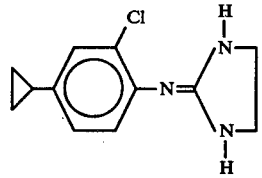

(I)

or a non-toxic, pharmacologically acceptable acid addition salt thereof.

2. A bradycardiac pharmaceutical composition consisting essentially of an inert pharmaceutical carrier and an effective bradycardiac amount of a compound of claim 1.

3. A method for slowing the heart rate of a warm-blooded animal in need thereof, which comprises orally, parentally, or rectally administering an effective bradycardiac amount of a compound of claim 1.

* * * * *